United States Patent [19]
Palmer et al.

[11] Patent Number: 5,191,888
[45] Date of Patent: Mar. 9, 1993

[54] ASSEMBLY OF AN EXTENSION GUIDEWIRE AND AN ALIGNMENT TOOL FOR SAME

[75] Inventors: Matthew Palmer, Miami; John J. Starkey, Cooper City; Fernando M. Viera, Hialeah, all of Fla.

[73] Assignee: Cordis Corporation, Miami Lakes, Fla.

[21] Appl. No.: 860,264

[22] Filed: Mar. 31, 1992

Related U.S. Application Data

[63] Continuation of Ser. No. 510,537, Apr. 18, 1990, abandoned, which is a continuation-in-part of Ser. No. 510,522, Apr. 18, 1990, Pat. No. 5,139,032, and a continuation-in-part of Ser. No. 510,523, Apr. 18, 1990, Pat. No. 5,113,872.

[51] Int. Cl.$^5$ .............................................. A61B 6/00
[52] U.S. Cl. .................................... 128/657; 128/772; 604/283
[58] Field of Search ............... 128/657, 658, 772, 912; 604/283, 905; 285/27

[56] References Cited

U.S. PATENT DOCUMENTS

| | | | |
|---|---|---|---|
| 4,509,944 | 4/1985 | King et al. | 604/164 X |
| 4,827,941 | 5/1989 | Taylor et al. | 128/657 |
| 4,860,757 | 8/1989 | Lynch et al. | 128/657 |
| 4,875,489 | 10/1989 | Messner et al. | 128/772 |

OTHER PUBLICATIONS

Constantin Cope MD "Guide Wire Extension" *Radiology*, Sep. 24, 1985, 157: 263.

*Primary Examiner*—Max Hindenburg
*Attorney, Agent, or Firm*—Henry W. Collins; Thomas R. Vigil

[57] ABSTRACT

The alignment tool is used to align the proximal end of a medical catheter wire with connecting means at the distal end of an extension wire. The alignment tool comprises a body having passage means therethrough including first and second inlet means for receiving and guiding into each end, respectively, of said passageway the proximal end of the medical catheter wire and the connecting means at the distal end of the extension wire. The alignment tool is preferably mounted in an extension wire dispensing assembly including means for receiving and holding a length of extension wire and a holder mounted to the dispensing means and having means for receiving and holding the alignment tool. The dispensing means include a coiled tube.

10 Claims, 2 Drawing Sheets

5,191,888

ASSEMBLY OF AN EXTENSION GUIDEWIRE AND AN ALIGNMENT TOOL FOR SAME

This is a continuation of application Ser. No. 07/510,537 filed Apr. 18, 1990 now abandoned which is a continuation-in-part of application Ser. Nos. 07/510,522 filed Apr. 18, 1990 and now U.S. Pat. No. 5,139,032 and 07/510,523 filed Apr. 18, 1990 now U.S. Pat. No. 5,113,872.

BACKGROUND OF THE INVENTION

1. Field of the Invention

The present invention relates to an improved alignment tool which is mounted in a holder that holds portions of a coiled tube which forms part of a coiled tube dispensing assembly that receives an extension guidewire therein.

2. Description of the Related Art Including Information Disclosed Under 27 CFR §§ 1.97-1.99

Heretofore, it has been proposed to provide an extension wire or guidewire which is connected to the proximal end of a shorter initially inserted guidewire or cut proximal end of a fixed balloon on a guidewire to facilitate the removal and insertion of a new balloon, such as by means of a guiding catheter, into and through the femoral artery or carotid artery to the heart or other location where an area of stenotic buildup exists so that that location or position of the first inserted balloon is not lost while a new dilatation catheter or new fixed balloon on a guidewire is inserted to the location of the stenotic build-up.

For example, there is proposed in U.K. Patent Application No. 2 180 454 A, guidewire system where the proximal end of an initially inserted guidewire is received in a sleeve which is also received over the distal end of an extension wire and the sleeve is crimped to fix the mating ends of the guidewire and extension wire together.

Also, an extendable guidewire system has been proposed in U.S. Pat. No. 4,827,941 wherein a small diameter proximal end portion of a primary guidewire is frictionally received within a tubular member fixed to a distal end of a guidewire extension section.

Further, an extendable guidewire for introducing a dilatation catheter into a cardiovascular system has been proposed in U.S. Pat. No. 4,875,489 where the proximal end of a main guidewire has a tapered end portion which is received into a tubular member having a slit or slot therein which permits it to expand, the tubular member being received within an outer sleeve and fixed to a reduced in diameter distal end of a section of an auxiliary guidewire.

However, such prior art extendable guidewire systems did not teach or provide for an alignment tool for assuring alignment of a connector assembly at the distal end of an extension wire with the proximal end of a guidewire or with a cut proximal end of a fixed balloon on a guidewire as the connector assembly and the guidewire proximal end or the cut proximal end of a fixed balloon on a guidewire are brought together.

As will be described in greater detail hereinafter, the alignment tool of the present invention provides a simple inexpensive and effective means for guiding the connector assembly at the distal end of an extension wire into engagement with a proximal end of an initially inserted guidewire or of an initially inserted and subsequently cut proximal end of a fixed balloon on a guidewire. Also, the alignment tool, when mounted to a coiled dispensing tube, greatly simplifies the task of a medical practitioner in connecting the proximal end of the guidewire or of a cut proximal end of a fixed balloon on a guidewire to a connector assembly at the distal end of the extension wire.

SUMMARY OF THE INVENTION

According to the present invention, there is provided an assembly of an extension wire and an alignment tool for aligning the proximal end of a medical catheter wire with connecting means at the distal end of an extension wire or at the proximal end of the medical catheter wire. The alignment tool comprises a body having (a) enlarged end portions, (b) a smaller-in-cross-section middle portion so that the large end portions define abutment means facing inwardly of the body toward and middle portion, and (c) passage means extending through the body along a longitudinal axis of the body and including a middle, generally cylindrical portion of substantially uniform diameter and first and second inlet means for receiving and guiding into each end, respectively, of the passageway and into the middle portion both the proximal end of a medical catheter wire or the distal end of the extension wire and the connecting means at the distal end of the extension wire or at the proximal end of the medical catheter wire, each of said inlet means at each end of the passage means of the alignment tool extending along the longitudinal axis and including an outwardly opening passage opening onto one of two opposite end faces of the body, and the body of the alignment tool being generally cylindrical in shape with the middle cylindrical portion of uniform diameter and with the opposite end faces facing outwardly and each lying in a plane generally normal to the longitudinal axis, the enlarged end portions comprising generally frusto-conical end portions each tapering or flaring radially outwardly from one of the end faces and axially toward the other end portion to an axially facing annular surface extending radially outwardly from the middle uniform diameter portion, the axially facing annular surfaces defining the abutment means.

The alignment tool can be part of an extension wire dispensing assembly including means for receiving and holding a length of extension wire and a holder mounted to the dispensing means and having means for receiving and holding the alignment tool. The receiving means can be a coiled tube.

DESCRIPTION OF THE PREFERRED EMBODIMENTS

Figure 1:
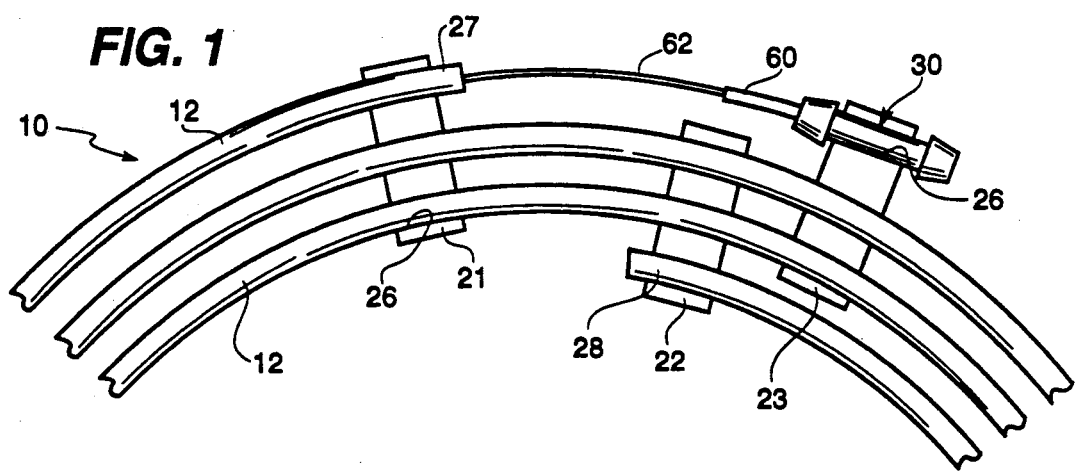
FIG. 1 is a fragmentary plan view of a portion of a coiled tube having mounted therein an extension guidewire and connector assembly and shows a holder mounted to the coiled tube for holding an alignment tool constructed according to the teachings of the present invention.
Figure 2:
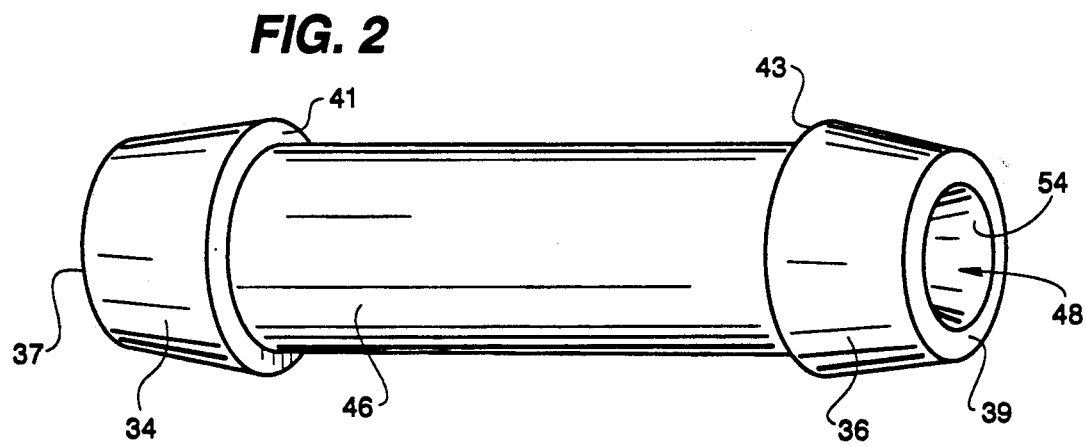
FIG. 2 is a perspective view of the improved alignment tool of the present invention.
Figure 3:
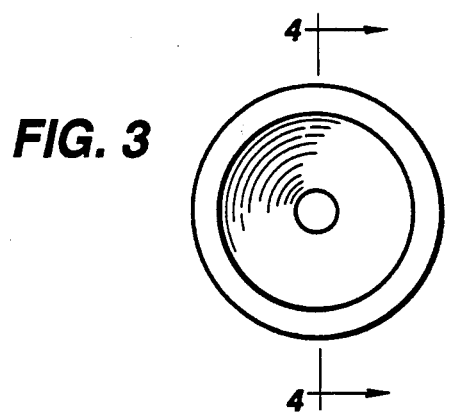
FIG. 3 is an end view of the alignment tool shown in FIG. 2.

In FIG. 1 there is illustrated a fragmentary portion of a coiled tube assembly 10 including a coiled dispensing tube 12 with sections thereof held in a coiled arrangement by holders 21, 22 and 23 each having three (3) slots 26 for engaging sections of the coiled dispensing tube 12.

The holder 21 mounts the inner proximal end 27 of the tube and the holder 22 holds the outer distal end 28 of the dispensing tube 12. The ends 27 and 28 are spaced circumferentially a short distance apart. The holder 23 is mounted to the coiled dispensing tube 12 circumferentially to one side of both of the holders 21 and 22 and has mounted therein an alignment tool 30 constructed according to the teachings of the present invention and located circumferentially a short distance from the outer distal end of 28 of the dispensing tube 12.

The alignment tool 30 and its mounting to the coiled tube 12 according to the teachings of the present invention facilitate and simplify the connecting of the proximal end of a guidewire or cut proximal end of a fixed balloon on a guidewire to an extension wire received and stored in the dispensing tube 12.

The provision of an alignment tool for facilitating the connection of a proximal end of a, guidewire to an extension wire is disclosed in U.S. Ser. No. 07/510,523 for: GUIDEWIRE EXTENSION SYSTEM and filed concurrently herewith, of which this application is a continuation-in-part and the disclosure of which is incorporated herein by reference.

The provision of an alignment tool for facilitating the connection of a cut proximal end of a fixed balloon on a guidewire to an extension wire is disclosed in U.S. Ser. No. 07/510,522 for: FIXED BALLOON ON A GUIDEWIRE EXTENSION WIRE KIT AND METHOD and filed concurrently herewith, of which this application is a continuation-in-part and the disclosure of which is incorporated herein by reference.

As shown in FIGS. 1-5, the alignment tool 30 includes a generally cylindrical body 32 having enlarged ends 34 and 36 much like a "dumb bell." Each of the enlarged ends 34,36 is generally frusto-conical, tapering axially inwardly and outwardly from an outer end surface 37 or 39 to an annular shoulder 41 or 43. A middle portion 46 of the body 32 between the annular shoulders is cylindrical.

Figure 4:
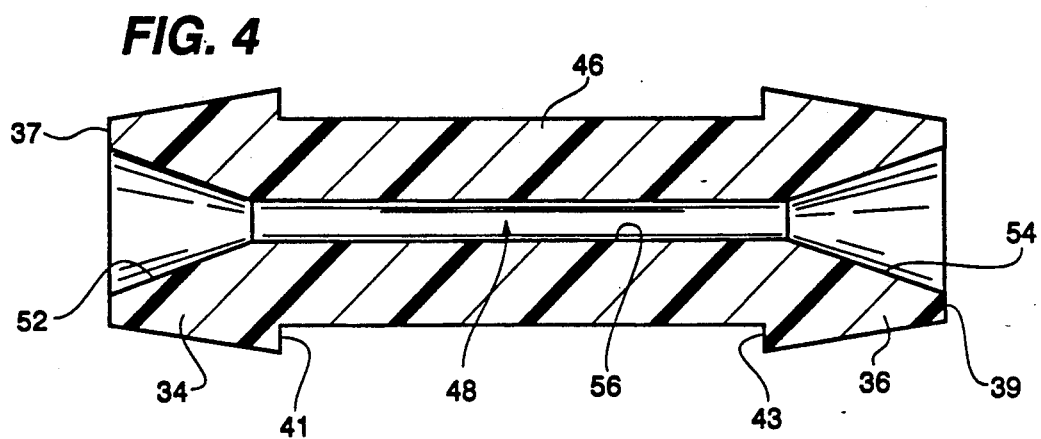
FIG. 4 is a longitudinal sectional view of the alignment tool and is taken along line 4—4 of FIG. 3.
Figure 5:
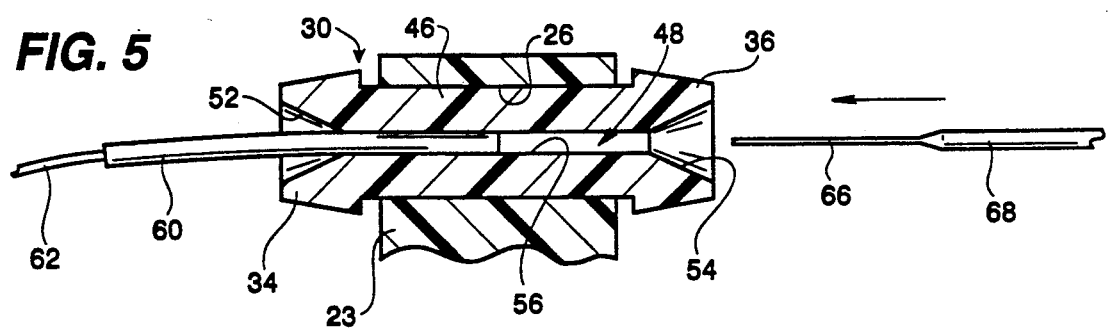
FIG. 5 is a fragmentary longitudinal sectional view through the alignment tool as mounted in the holder shown in FIG. 1 and shows a tube of a connector assembly at the distal end of an extension wire received in one end of the alignment and a ground down distal end of a guidewire of a dilatation balloon catheter and guidewire assembly positioned for insertion into the alignment tool.

As shown in FIGS. 4 and 5, the body has a throughbore 48 which extends axially therethrough and which has tapered or flared end portions 52,54 which extend axially and radially outwardly from a central uniform diameter portion 56 of the throughbore 48 to one of the end surfaces 37,39.

Referring now to FIG. 5, the alignment tool 30 has the middle portion 46 of the body 32 mounted in one of the slots 26 in the holder 23, with the annular shoulders 41,43 preventing the tool 30 from being pulled axially out of the slot 26.

Figure 6:
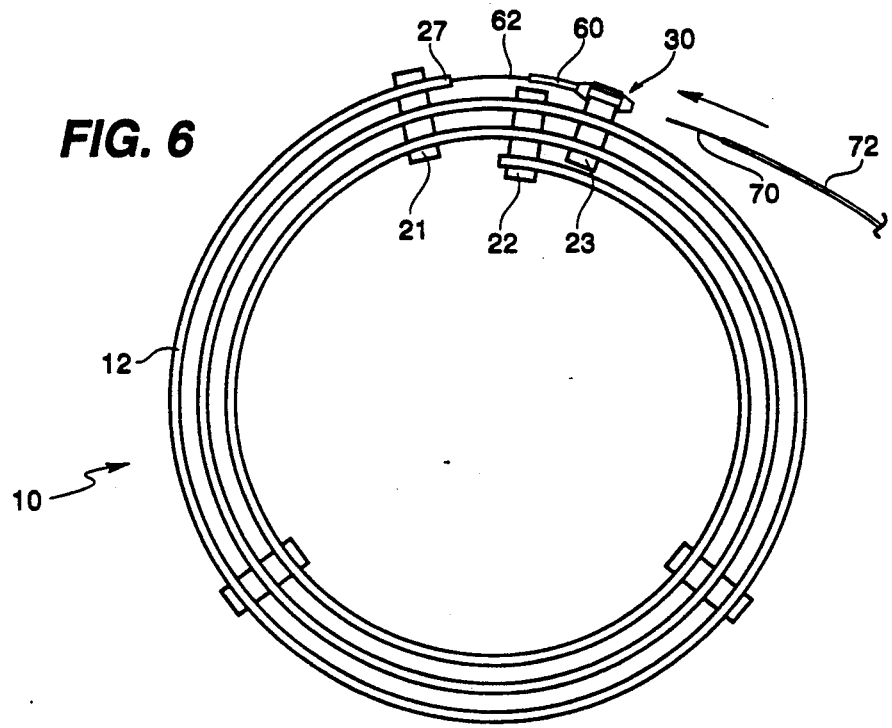
FIG. 6 is a plan view of the coiled tube assembly with the extension wire mounted therein and shows a tube of the connector assembly received in the alignment tool which is mounted to the holder mounted on the coil tube and shows a cut proximal end of a fixed balloon on a guidewire positioned for insertion into the alignment tool.
Figure 7:
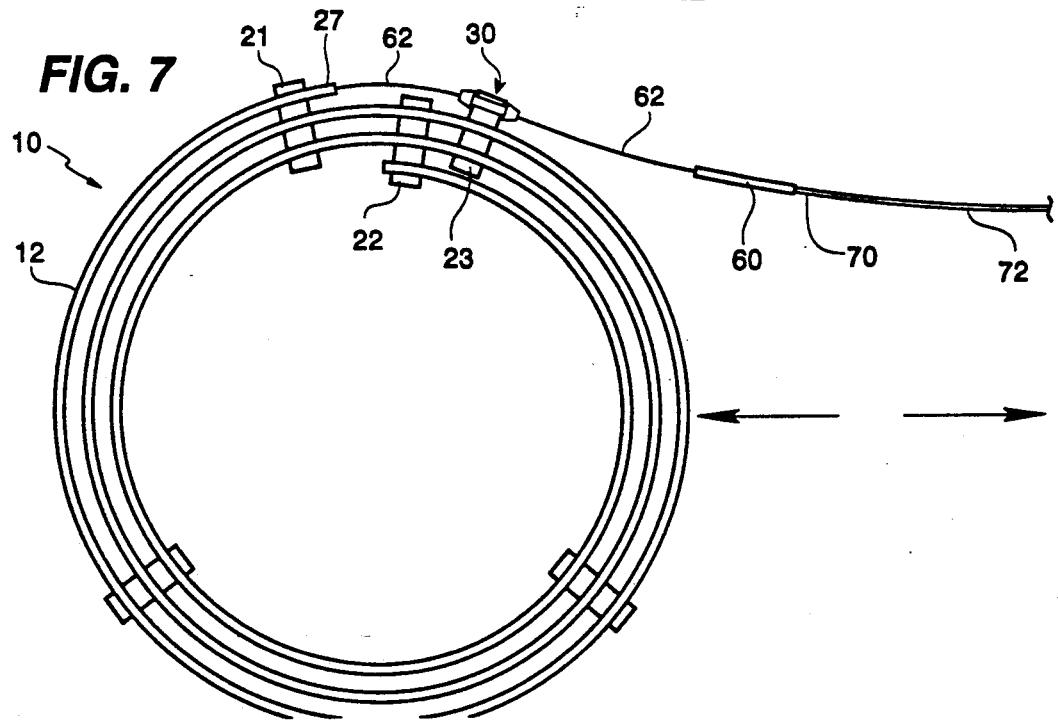
FIG. 7 is a plan view of the coiled tube, similar to the view shown in FIG. 6 and shows the cut proximal end of a fixed balloon on a guidewire or a proximal end of a guidewire of a balloon catheter and guidewire assembly mounted in the tube of the connector assembly and shows relative movement between the coiled tube and the connector assembly for withdrawing or pulling out the extension wire from the coiled tube assembly.

Then, the tapered end portions 52,54 of the throughbore 48 facilitate the insertion, at one end thereof, of a tubular connector assembly 60 at the distal end 62 of an extension wire 64 and, at the other end thereof, the ground-down proximal end 66 of a guidewire 68 (FIG. 5) or the cut proximal end 70 of a fixed balloon on a guidewire 72 (FIG. 6).

Typically, the tubular connector assembly 60 is prelocated through the tapered end portion 52 and within the alignment tool 30 throughbore 48 half-way through the alignment tool 30 as shown in FIG. 5.

Then, in use, the ground-down distal end 66 of the guidewire 68 is inserted into the other tapered end portion 54 of the alignment tool 30 mounted in the holder 23 fixed to the coiled dispensing tube 12 and guided into the uniform diameter portion 56 of the throughbore 48, into the tubular connector assembly 60 and locked therein in the manner disclosed in copending Application.

Alternatively, the cut proximal end 70 of the fixed balloon on a guidewire 72 can be inserted through the tapered end portion 52 into the throughbore 48, into the tubular connector assembly 60 as shown in FIG. 6 and then locked in place as disclosed in co-pending Application Ser. No.

Once the proximal end 66 of the guidewire 68 or the cut proximal end 70 of a fixed balloon on a guidewire 72 is connected by means of the connector assembly 60 to the distal end 62 of the extension wire 64, relative movement between the connected proximal end 66 or 70 of the guidewire 68 or fixed balloon on a guidewire 72 and the coiled tube assembly 10 causes the extension wire 64 to be pulled out and dispensed from the coiled dispensing tube 12. Then a guiding catheter (not shown) can be inserted over the extension wire 64 and the assembly 10 causes the extension wire 64 to be pulled out and dispensed from the coiled dispensing tube 12. Then a guiding catheter (not shown) can be inserted over the extension wire 64 and the initially inserted guidewire 68 or fixed balloon on a guidewire 72 for effecting replacement of a dilatation balloon catheter or of the fixed balloon on a guidewire 72 without loss of location of the initial position of the balloon of either catheter.

It is also contemplated that the location of the connector assembly 60 can be reversed and mounted on the proximal end 66 of a guidewire 68 which then can be inserted into the alignment tool 30 for connecting with a distal end of an extension wire 64 received in the throughbore 48.

From the foregoing remarks it will be appreciated that the alignment tool 30 and its mounting to the coiled tube 12 greatly simplify the task of connecting an extension wire 64 to a guidewire 68 or to a cut fixed balloon on a guidewire 72.

Since the alignment tool 30 is preferably provided already mounted such as by being snap-fitted or clipped in place in the holder 23 with the connector assembly 60 of the extension wire 64 pre-positioned therein, all that is necessary for the medical practitioner to do is to insert the proximal end 66 of a guidewire 68 or a cut proximal end 70 of a fixed balloon on a guidewire 72 into the tool 30 and then pull out the proximal end 66 or 70 connected to the extension wire 64 thereby to pull the extension wire 64 through the tool 30 until it is free of the coiled dispensing tube 12.

When the alignment tool 30 is an integral part of the coiled dispensing tube assembly 10 as described above, it is essentially invisible to the user.

It will be understood that modifications can be made to the alignment tool 30 of the present invention and its mounting to the coiled dispensing tube 12 without departing from the teachings of the present invention. Also, it will be understood that the alignment tool 30 and its manner of mounting to the coiled tube 12 have a number of advantages some of which have been described above and others of which are inherent in the invention. Accordingly, the scope of the invention is only to be limited as necessitated by the accompanying claims.

We claim:

1. An assembly of an extension wire and an alignment tool for aligning the proximal end of a medical catheter wire with connecting means at the distal end of said extension wire or at the proximal end of the medical catheter wire, said alignment tool comprising a body having (a) enlarged end portions, (b) a smaller-in-cross-section middle portion so that said large end portions define abutment means facing inwardly of said body toward said middle portion, and (c) passage means extending through said body along a longitudinal axis of said body and including a middle, generally cylindrical portion of substantially uniform diameter and first and second inlet means for receiving and guiding into each end, respectively, of said passageway and into said middle portion both the proximal end of a medical catheter wire or the distal end of said extension wire and the connecting means at the distal end of the extension wire or at the proximal end of the medical catheter wire, each of said inlet means at each end of the passage means of the alignment tool extending along the longitudinal axis and including an outwardly opening passage opening onto one of two opposite end faces of the body, and the body of the alignment tool being generally cylindrical in shape with the middle cylindrical portion of uniform diameter and with the opposite end faces facing outwardly and each lying in a plane generally normal to the longitudinal axis, the enlarged end portions comprising generally frusto-conical end portions each tapering or flaring radially outwardly from one of the end faces and axially toward the other end portion to an axially facing annular surface extending radially outwardly from the middle uniform diameter portion, the axially facing annular surfaces defining the abutment means.

2. The assembly of an extension wire and an alignment tool for aligning the proximal end of a medical catheter wire with connecting means at the distal end of said extension wire or at the proximal end of the medical catheter wire, said alignment tool comprising a body having (a) enlarged end portions, (b) a smaller-in-cross-section middle portion so that said large end portions define abutment means facing inwardly of said body toward said middle portion, and (c) passage means extending through said body along a longitudinal axis of said body and including a middle, generally cylindrical portion of substantially uniform diameter and first and second inlet means for receiving and guiding into each end, respectively, of said passageway and into said middle portion both the proximal end of a medical catheter wire or the distal end of said extension wire and the connecting means at the distal end of the extension wire or at the proximal end of the medical catheter wire, and an extension wire dispensing assembly including dispensing means for receiving and holding a length of extension wire and a holder mounted to said dispensing means and having means for receiving and holding said alignment tool.

3. The assembly of claim 2 wherein each of said inlet means at each end of said passage means of said alignment tool include an outwardly opening passage, opening on to one of two opposite end surfaces of said body.

4. The assembly of claim 2 wherein each inlet means of said alignment tool extends along said longitudinal axis and is defined by a generally frusto-conical opening passage or outwardly opening passage, opening generally radially outwardly from and along said longitudinal axis.

5. The assembly of claim 2 wherein said body of said alignment tool is generally cylindrical in shape with a middle cylindrical portion of uniform diameter and opposite end faces facing outwardly and lying in a plane generally normal to said longitudinal axis, said enlarged end portions comprising generally frusto-conical end portions each tapering or flaring radially outwardly from one of said end faces and axially toward the other end portion to an axially facing annular surface extending radially outwardly from said middle uniform diameter portion, said axially facing annular surfaces defining said abutment means.

6. The assembly of claim 2 wherein said dispensing means includes a coiled tube held in a coiled tube assembly by several holders and having received therein the extension wire.

7. The assembly of claim 2 wherein said holder has a slot into which said alignment tool is received, said holder having wall surfaces adjacent the opposite ends of said slot and said body of said alignment tool having abutment means facing said wall surfaces and being capable of engaging said wall surfaces upon axial movement of said body thereby preventing said alignment tool from being axially pulled out of said slot.

8. The assembly of claim 2 further including an extension wire mounted in said dispensing means and having connecting means at the distal end thereof.

9. The assembly of claim 8 wherein the distal end of the extension wire extends outwardly from said dispensing means such that the connecting means thereon are received and held within said passage means of said alignment tool.

10. The assembly of claim 8 wherein said connector means includes a small diameter tube with means therein for engaging the proximal end of a guidewire of a dilatation balloon catheter assembly of a proximal end of a fixed balloon on a guidewire.

* * * * *